United States Patent
Castro-Perez et al.

(10) Patent No.: US 7,189,964 B2
(45) Date of Patent: Mar. 13, 2007

(54) SYSTEM AND METHOD FOR ISOTOPIC SIGNATURE AND MASS ANALYSIS

(75) Inventors: Jose Castro-Perez, Manchester (GB); Robert Plumb, Milford, MA (US); Christopher Jones, Macclesfield (GB)

(73) Assignee: Waters Investments Limited, New Castle, DE (US)

( * ) Notice: Subject to any disclaimer, the term of this patent is extended or adjusted under 35 U.S.C. 154(b) by 0 days.

(21) Appl. No.: 11/315,844

(22) Filed: Dec. 22, 2005

(65) Prior Publication Data

US 2006/0169885 A1    Aug. 3, 2006

Related U.S. Application Data

(63) Continuation of application No. PCT/US04/21248, filed on Jul. 2, 2004.

(60) Provisional application No. 60/485,278, filed on Jul. 3, 2003.

(51) Int. Cl.
*H01J 49/40* (2006.01)
(52) U.S. Cl. .................. 250/282; 250/281; 702/22
(58) Field of Classification Search ............. 250/282, 250/281; 702/22, 23, 27, 28, 30
See application file for complete search history.

(56) References Cited

U.S. PATENT DOCUMENTS

| | | | |
|---|---|---|---|
| 6,147,344 A | 11/2000 | Annis et al. | |
| 6,207,861 B1 | 3/2001 | Nash et al. | |
| 6,329,146 B1 | 12/2001 | Crooke et al. | |
| 6,475,807 B1 | 11/2002 | Geysen et al. | |
| 7,112,784 B2 * | 9/2006 | Bateman et al. | ............ 250/282 |
| 2001/0019107 A1 | 9/2001 | Maekawa et al. | |
| 2003/0001090 A1 | 1/2003 | Ranasinghe et al. | |

FOREIGN PATENT DOCUMENTS

WO    WO 89/12312 A    12/1989

* cited by examiner

*Primary Examiner*—Kiet T. Nguyen
(74) *Attorney, Agent, or Firm*—Anthony J. Janiuk; Jamie H. Rose

(57) ABSTRACT

Mass intensity values, isotopic ratios and exact mass differences between isotopes may be obtained and analyzed to determine if there are one or more masses of interest. In one implementation, a method will look among the mass intensity values for peaks of interest. The mass intensity values, representative of isotopic signatures, will be compared to a criteria in order to determine which of the masses are of interest. Although the invention is not so limited, examples of such criteria include mass intensity values above a specified threshold, within a certain ratio of another mass intensity value, and/or separation between the masses themselves. Optionally, a tolerance may be applied to the criteria. If masses are found to be of interest, MS/MS can automatically be triggered for one or all of the masses of interest, when an analyzing system such as an LC-MS-MS, GC-MS-MS or MALDI-MS-MS system is used.

23 Claims, 10 Drawing Sheets

| Field | Range | Default Value | Units |
|---|---|---|---|
| Use Isotopic Pattern Identification | True, False | False | / |
| First Mass Difference | 0.001 - 5.0 | 2 | Da |
| First Ratio | 99:99 | 1:1 | / |
| Use Second Mass Difference | True, False | False | Da |
| Second Mass Difference | 0.001 - 5.0 | 2.0 | Da |
| Second Ratio | 99:99 | 1:1 | / |
| Mass Tolerance | 0.001 - 1.000 | 0.5 | mDa |
| Ratio Tolerance | 1 - 100 | 30 | % |
| Peak Threshold | 1 - 100000 | 10 | counts/sec |
| Use Intensity Ratios | True, False | True | / |

SYSTEM AND METHOD FOR ISOTOPIC SIGNATURE AND MASS ANALYSIS

CROSS REFERENCE TO RELATED APPLICATIONS

This application claims benefit of and is a continuation of International Application No. PCT/US2004/021248, filed Jul. 2, 2004 and designating the United States, which claims benefit of a priority to U.S. Provisional Application No. 60/485,278, filed Jul. 3, 2003. The contents of these applications are expressly incorporated herein by reference in its entirety.

FIELD OF THE INVENTION

The illustrative embodiment of the present invention relates generally to isotopic signature analysis and the use of mass spectrometry in combination with isotopic signature analysis.

BACKGROUND OF THE INVENTION

Chromatography separates the individual components contained within a sample so that they may be identified. For example, in liquid chromatography two phases are involved, a mobile phase and a stationary phase. A liquid sample mixture (the "mobile phase") is passed through a column packed with particles (the "solid phase") in order to effect a separation of the constituent components. The particles in the column may or may not be coated with a liquid designed to react with the mobile phase. The constituent components in the mobile phase, i.e. in the sample, pass through the packed column at different rates based upon a number of factors. The separation of the sample into its constituent components is then analyzed by observing the sample as it exits the far end of the column.

The speed with which the different constituent components pass through the column depends on the interaction of the mobile phase with the solid phase. The components in the sample may physically interact with the particles or a substance coating the particles such that their movement through the column is retarded. Different components in the sample being analyzed will react differently to the particular particle and/or coating by interacting with the particular particles and/or coating with differing degrees of strength depending upon the chemical makeup of the component. Those components which tend to bond more strongly to the particles and/or coating will pass through the column more slowly than those components which bond weakly or not at all with the particle/coating. In addition to chemical reactions, the size of the components in the sample may dictate the speed with which they pass through the column. For example, in gel-permeation chromatography, different molecules in the solution being analyzed pass through a matrix containing pores at different speeds thereby effecting a separation of the different molecules in the sample. In size exclusion chromatography the size of the particles and their packing method in the column combine with the size of the components in the sample to determine the rate at which a sample passes through the column (as only certain size components may easily traverse the gaps/interstitial spaces between particles).

The separated sample travels into a detector at the far end of the column where the retention time is calculated for the various components in the sample. The retention time is the time required for the sample to travel from the injection port (where the sample is introduced into the column) through the column and to the detector. The amount of the component exiting the solid phase may be graphed against the retention time to form a chart with peaks which are known as chromatographic peaks. The peaks identify the different components.

The separated components may be fed into a mass spectrometer for further analysis in order to determine their chemical make-up. Systems with two mass spectrometer stages are referred to as LC-MS-MS systems. A mass spectrometer takes a sample as input and ionizes the sample to create positive ions. A number of different ionization methods may be used including the use of an electronic beam. The positive ions are then separated by mass in a first stage separation commonly referred to as MS1. The mass separation may be accomplished by a number of means including the use of magnets which divert the positive ions to differing degrees based upon the weight of the ions. The separated ions then travel into a collision cell where they come in contact with a collision gas or other substance which interacts with the ions. The reacted ions then undergo a second stage of mass separation commonly referred to as MS2.

The separated ions are analyzed at the end of the mass spectrometry stage or stages. The analysis graphs the intensity of the signal of the ions versus the mass of the ion in a graph referred to as a mass spectrum. The analysis of the mass spectrum gives both the masses of the ions reaching the detector and the relative abundances. The abundances are obtained from the intensity of the signal. The combination of liquid chromatography with mass spectrometry may be used to identify chemical substances such as, for example, metabolites. When a molecule loses electrons, covalent bonds often break, resulting in an array of positively charged fragments. The mass spectrometer measures the masses of the fragments which may then be analyzed to determine the structure and/or composition of the original molecule. The information may be used to isolate a particular substance in a sample.

Metabolism may be defined as the chemical changes that take place in a cell or an organism that are used to produce energy and the basic materials which are needed for life processes such as mitosis. The byproducts of the chemical reaction may be referred to as metabolites. By analyzing and identifying the metabolites that are present in a sample, it is possible to determine the route of metabolism. For example, an analysis of metabolites in urine may be used to determine what substances were ingested by the individual that produced the urine. The identification and analysis of the metabolites is often performed using liquid chromatography in combination with mass spectrometry.

Conventionally, the analysis of metabolites involves three separate sample runs. The first sample run is a control. Following the control sample run a first analyte sample run is conducted. The chromatographic peaks from the analyte sample results are compared to the chromatographic peaks of the control and the results of the comparison are used to eliminate the components that appear in both samples. A second analyte sample run is then conducted that focuses on the components unique to the analyte sample in order to identify unexpected metabolites that appear in the analyte sample but not in the control sample. Unfortunately, the comparison of the control sample to the first analyte sample is a time intensive procedure requiring in most cases direct human participation.

SUMMARY OF THE INVENTION

The illustrative embodiment of the present invention provides an automated mechanism for detection and analysis of isotopic signatures of interest. In one implementation, a method will look among the mass intensity values for peaks of interest. The mass intensity values, representative of isotopic signatures, will be compared to a criteria in order to determine which of the masses are of interest. In one implementation, the criteria includes isotopic ratios and mass differences between isotopes corresponding to the same compound. If masses are found to be of interest, MS/MS can automatically be triggered for one or all of the masses of interest.

In one embodiment, a method is provided for use with an analysis system for analysis of isotopic signatures with masses. The method includes the step of obtaining mass intensity values corresponding to a plurality of masses. The mass intensity values are compared to a criteria to determine whether any of the plurality of masses are of interest. If any masses are of interest, a mass spectrometry process is directed to be performed on the masses of interest. A further embodiment of the invention provides a medium holding computer executable steps for the method.

Another embodiment of the invention provides a system for analysis of isotopic signatures with mass. The system includes an electronic device for obtaining mass intensity values corresponding to masses. The electronic device can compare the plurality of mass intensity values to a criteria to determine whether any of the plurality of masses are of interest. A second stage mass separation device is also provided to perform mass spectrometry on any of the masses that are of interest.

BRIEF DESCRIPTION OF THE DRAWINGS

The invention will be apparent from the description herein and the accompanying drawings, in which like reference characters refer to the same parts throughout the different views.

FIG. 11 provides a table having sample default values according to the illustrative embodiment of the invention;

FIG. 12 provides a further table of a user interface according to an implementation of the illustrative embodiment of the invention.

DETAILED DESCRIPTION

The present invention is directed toward analysis of a plurality of mass intensity values to determine one or more masses of interest. According to an embodiment of the invention, a method will look among the mass intensity values for peaks of interest on a per scan basis while in mass spectrometry (MS) mode. The mass intensity values, representative of isotopic signatures, will be compared to a criteria in order to determine which of the masses are of interest. If masses are found to be of interest, MS/MS can automatically be triggered for one or all of the masses of interest. Although the invention is not so limited, examples of such criteria include mass intensity values above a specified threshold, within a certain ratio of another mass intensity value, and/or separation between the masses themselves. Optionally, a tolerance may be applied to the criteria.

Figure 1:
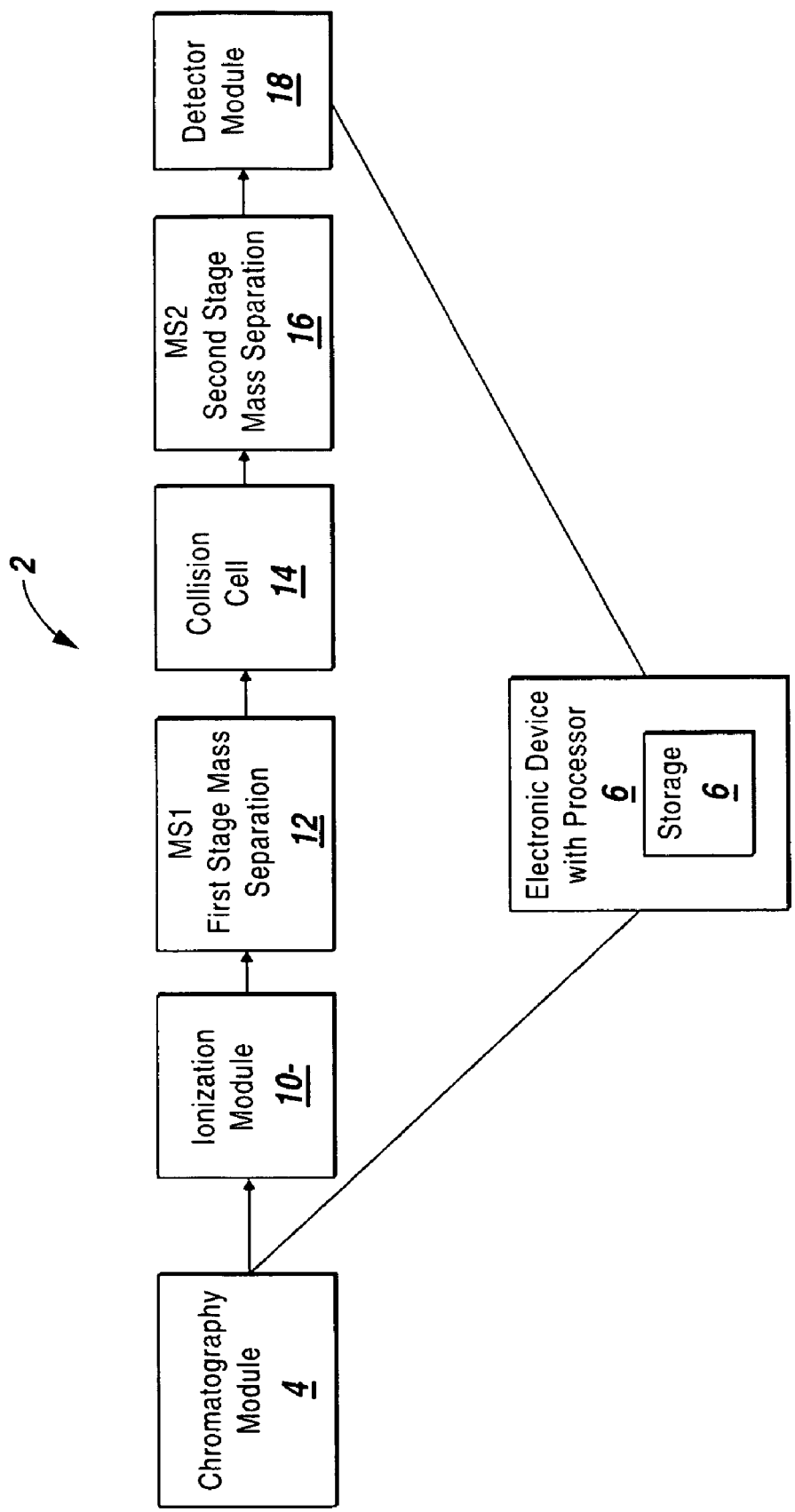
FIG. 1 depicts an environment suitable for practicing the illustrative embodiment of the present invention.

The present invention may be performed in an analyzing system such as an LC-MS-MS system as depicted by way of example in FIG. 1. Those skilled in the art will recognize that this approach could also be applied to other chromatographic techniques such as GC-MS-MS and MALDI-MS-MS (Matrix Assisted Laser Desorption/Ionization-Mass Spectroscopy-Mass Spectroscopy). According to the illustrative embodiment, the analyzing system 2 includes a chromatography module 4, such as a liquid chromatography module. Also included is an ionization module 10. The ionization module 10 receives as an input sample the output from the chromatography module 4. The ionization module performs ionization of the sample. Those skilled in the art will recognize that there are a number of different ways in which the sample may be ionized, such as by bombarding the sample with a stream of high energy electrons.

The ions produced by the ionization module 10 are passed on to the MS1 first stage mass separation module 12. The mass separation may be performed using any of a number of well-known techniques. For example, the ions may be subjected to magnetic forces which alter the path of the ions based upon the mass of the ion. The separated ions are then be passed into a collision cell module 14 where they are subjected to additional reactions, such as exposure of the ions to a gas designed to react with the separated ions. The sample may be further separated in an MS2 second stage mass separation module 16 prior to arriving at a detector module 18. The detector module 18 is used to generate a mass spectrum based on the detected signal generated by the exiting ions. Those skilled in the art will recognize that a number of different methods of mass separation may be used and different substances may be introduced into the collision cell 14 in order to react with the ions of particular interest. Similarly, the illustrative embodiment of the present invention may also be performed with a number of different metabolite analyzing systems.

According to the example, an electronic device with a processor 6 is interfaced with the detector module 18 and the chromatography module 4. The electronic device 6 may be a server, desktop computer system, laptop, mainframe, network attached device or some other similar device with a processor. The electronic device may also be integrated into one of the modules in the metabolite analyzing system 2 without departing from the scope of the present invention. The electronic device 6 includes storage 8 which is used to record the results of sample runs. Those skilled in the art will recognize that the storage 8 may be located in any location accessible to the metabolite analyzing system.

Figure 2:
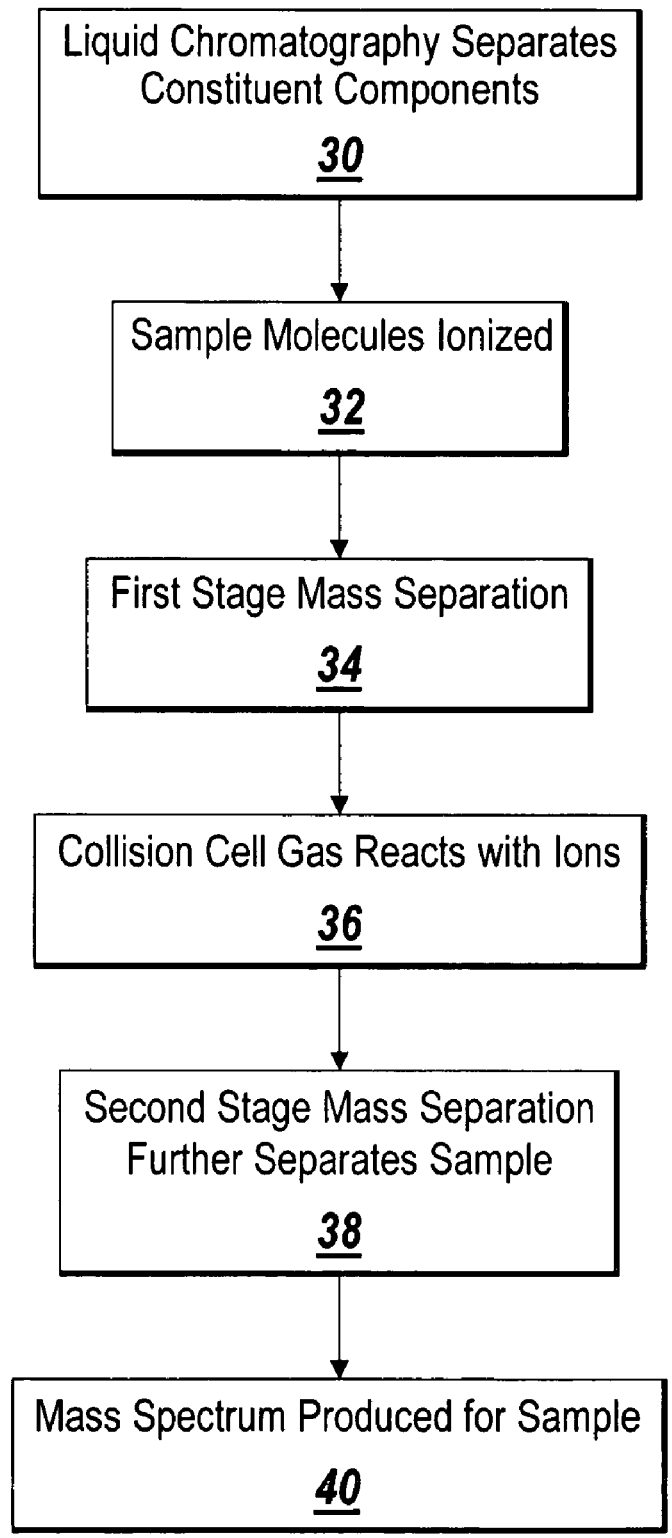
FIG. 2 is a flow chart of the sequence of steps used to perform liquid chromatography and mass spectrometry.

The sequence of steps performed to conduct a single LC-MS-MS run is depicted in the flow chart of FIG. 2. The sequence begins with a liquid chromatography separation of the components in a sample, step 30. The sample components exiting from the liquid chromatography system are passed into the ionization module 10 where ionization is performed, step 32. The first stage of mass separation is performed, step 34, and the separated ions are passed into the collision cell where they react to the collision cell reactant, step 36. Second stage mass separation is then performed on the reacted ions exiting from the collision cell, step 38. The separated ions are passed into the detector module 18 where a mass spectrum is generated from collected data thereby enabling the identification of metabolites contained within the sample, step 40.

Embodiments of the invention can provide a more specific search for xenobiotics and biomarkers by data dependent acquisitions in LC-MS/MS, which processes a distinctive isotopic signature. For example, in a case of naturally occurring compounds having chlorine or bromine, derivatized compounds with a specific tag can reflect whether carboxylic acid or a carbohydrate and radio labeled compounds are present.

The invention can reduce the number of experiments needed to illuminate false positives. By way of example, having a definite isotopic signature can allow components of interest to be recognized while optionally discarding information related to other components not of interest. Examples of implementations of the invention include detecting and elucidating metabolic structures during a drug discovery and development process and other applications such as Metabonomics and Metabolomics.

According to one example implementation of an illustrative embodiment of the invention, an mass difference, such as an exact mass difference, provided by a MICROMASS® Q-Tof micro™ mass spectrometer, a member of the Qtof family of instruments available from Waters Corporation of Milford, Mass., can be used to determine the isotopically labeled compounds together with the isotopic ratio. Although the invention is not so limited, this implementation of the invention can be very beneficial in xenobiotic and endogenous biomarker detection and identification.

It is understood that a wide variety of mass spectrometers may be used. For example, a quadrupole or time of flight mass spectrometer may be used. According to one implementation, the invention may use exact mass provided by a time of flight mass spectrometer. As used herein, exact mass refers to a mass value having an accuracy of at least four decimal places. Although the invention is not so limited, examples of time of flight mass spectrometers include the Q-Tof family of instruments available from Waters Corporation of Milford, Mass.

Figure 3:
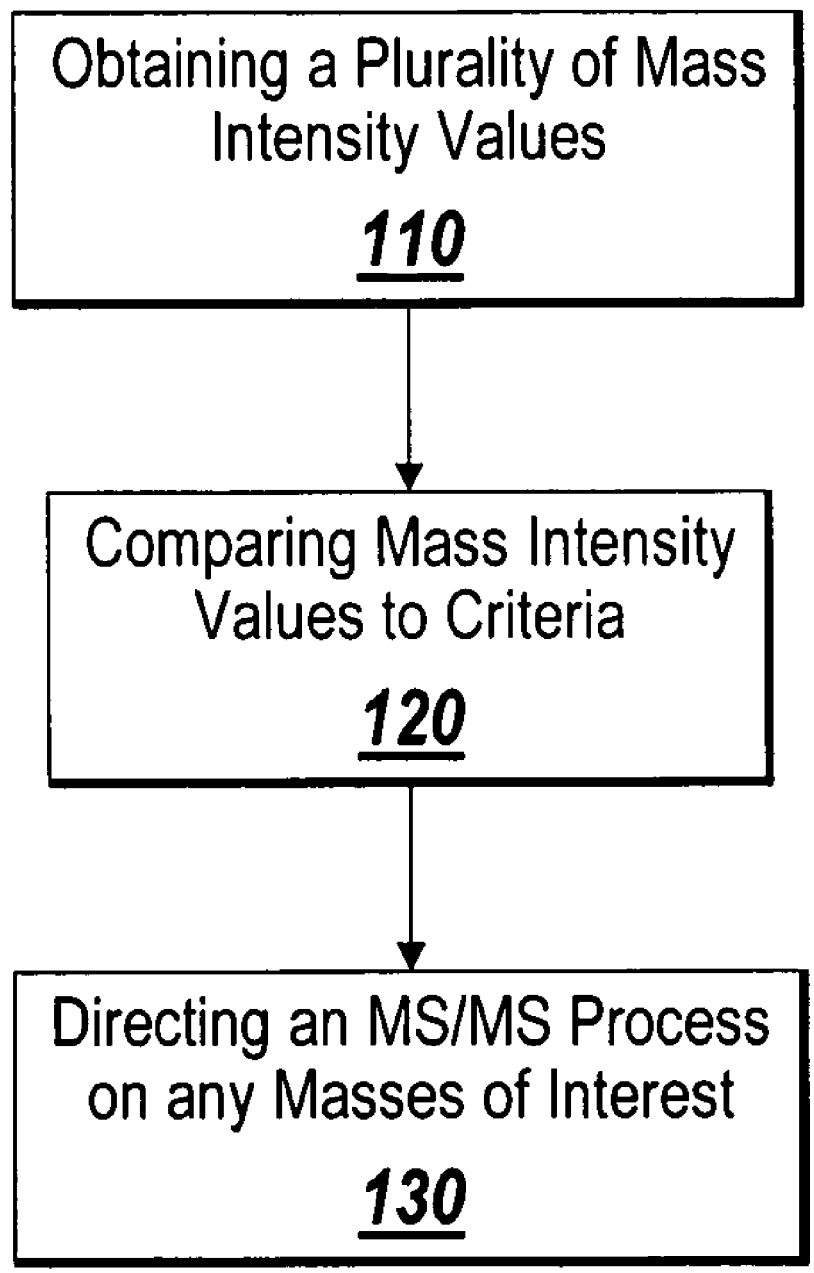
FIG. 3 illustrates a method according to the illustrative embodiment of the invention.
Figure 4:
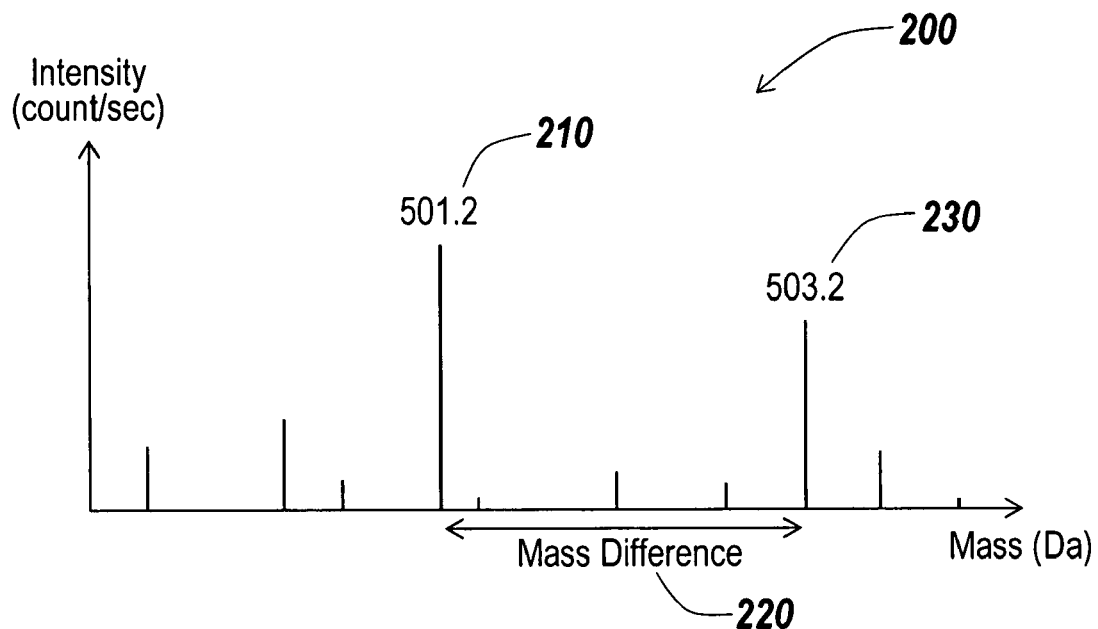
FIG. 4 provides a graph illustrating a first mass difference criteria according to the illustrative embodiment of the invention.

According to one embodiment of the invention, a method 100 is provided as illustrated by way of example in FIG. 3. A plurality of mass intensity values corresponding to a plurality of masses is obtained, step 110. The plurality of mass intensity values is compared to a criteria to determine whether any of the masses are of interest, step 120. A second mass spectrometry process may be performed on any of the masses that are of interest, step 130.

According to the illustrative embodiment, a wide variety of criteria are within the scope of the invention. Although the invention is not so limited, FIGS. 4–9 provide illustrations of various criteria that may be used alone or in combination. Each of FIGS. 4–9 illustrates a plurality of mass intensity values in a sample graphical form. Along a vertical axis is the intensity, in counts per second. Values of mass, in Daltons (Da), are provided along a horizontal axis. As illustrated in the graph 200 of FIG. 4, an example of a criteria is a first mass difference. According to this criteria, masses of interest may be specified by way of their difference in mass values. For example, on the graph 200, a first mass value 210 of 501.2 Da has a mass difference 220 of 2 Da from the second mass value 230 of 503.2 Da. In the event that a mass difference of 220 of 2 Da is specified as the first mass difference criteria, the second mass value 230 of 503.2 Da and the first mass value 210 of 501.2 Da would be determined to be masses of interest.

Figure 5:
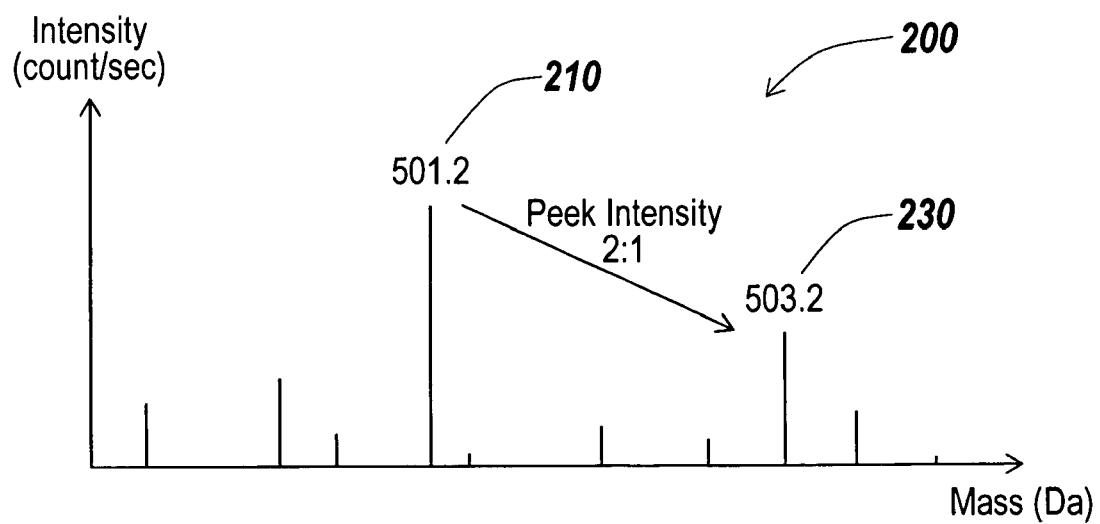
FIGS. 5 and 6 provide a graph illustrating a first ratio criterion according to the illustrative embodiment of the invention.
Figure 6:
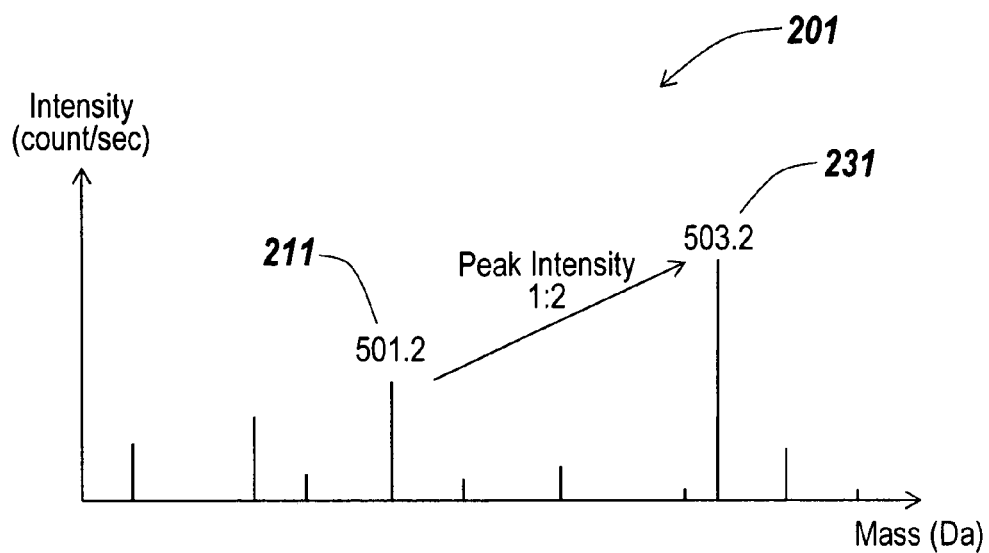

A second example criteria, a first ratio of intensities of mass values, is illustrated in the graph 200 of FIG. 5. An intensity of a first mass value 210 is compared to an intensity of a second mass value 230. By way of example, the first ratio can be specified as 2:1, and the intensities of the first mass value 210 and the second mass value 230 are compared. If the ratio of intensities matches the specified first ratio, in this case 2:1, the first mass value 210 of 501.2 Da and the second mass value 230 of 503.2 Da are determined to be masses of interest. If the detected intensity values of the masses do not match the specified first ratio, then the masses are not considered to be of interest. A second example of the first ratio is illustrated in the graph 201 of FIG. 6. The graph 201 provides a first mass value 211 of 501.2 Da and a second mass value 231 of 503.2 Da. In this case, if the first ratio is specified as 1:2, the mass values 211, 231 would be determined to be of interest.

Figure 7:
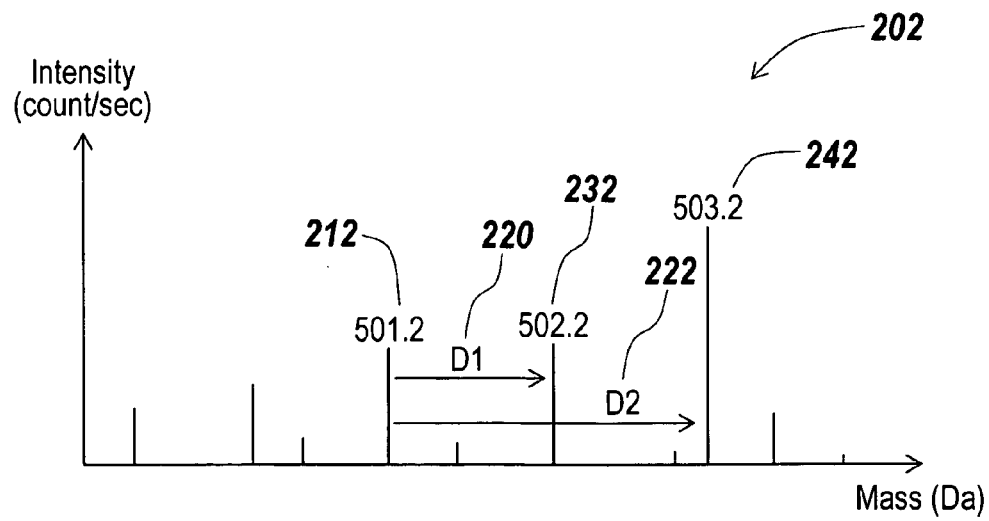
FIG. 7 provides a graph a second mass difference criterion according to the illustrative embodiment of the invention.
Figure 8:
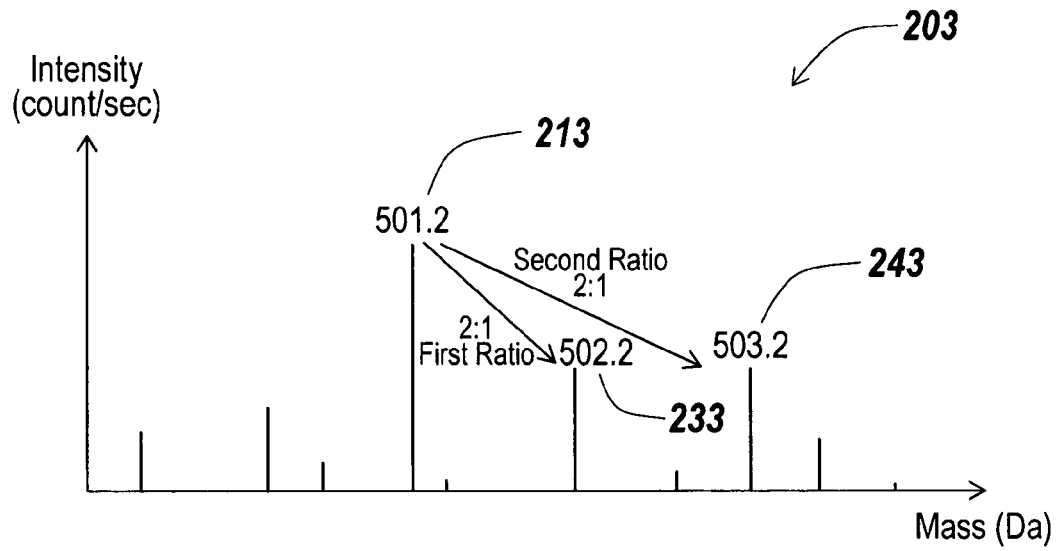
FIG. 8 provides a graph a second ratio criterion according to the illustrative embodiment of the invention.

Various criteria may also include comparing more than two mass values. FIGS. 7 and 8 illustrate variations of the mass difference and first ratio criteria that have been described in relation to FIGS. 4–6. The graph 202 of FIG. 7 illustrates a first mass value 212, a second mass value 232, and a third mass value 242. A first mass difference 220 is illustrated as D1, while a second mass difference 222 is illustrated as D2. When the second mass difference 222 is used as a criteria in addition to the first mass difference 220, both the first mass difference 220 and second mass difference 222 must match their predetermined criteria values in order to be considered as masses of interest.

FIG. 8 illustrates the use of a second ratio to the used as a criteria in addition to a first ratio. A graph 203 illustrates a first mass value 213, a second mass value 233, and a third mass value 243. In the illustrative example, a first ratio may be defined as the difference in intensity between the first mass value 213 and second mass value 233. A second ratio may be defined as the difference in intensity between the first mass value 213 and a third mass value 243. In this example, all three mass values will be considered to be of interest if criteria for the first ratio and second ratio are each 2:1, as the intensity of the first mass value 213 is twice each of the values of the second mass value 233 and third mass value 243. If either the first or second ratio does not meet the criteria, then none of the mass values would be considered to be of interest.

It is understood that tolerances may be applied to both ratio and mass difference values, to enable a range of data to be considered to match the criteria and be considered mass values of interest. By way of example, a mass tolerance window may be provided to allow for two different mass values to be considered masses of interest by allowing a mass tolerance to be specified. Similarly or alternatively, a ratio tolerance may be specified to allow for minor discrepancies in intensity of mass values to still be considered to be items of interest. Tolerance values can be applied both in cases where only two mass intensity values are compared or a plurality of mass intensity values is compared.

Figure 9:
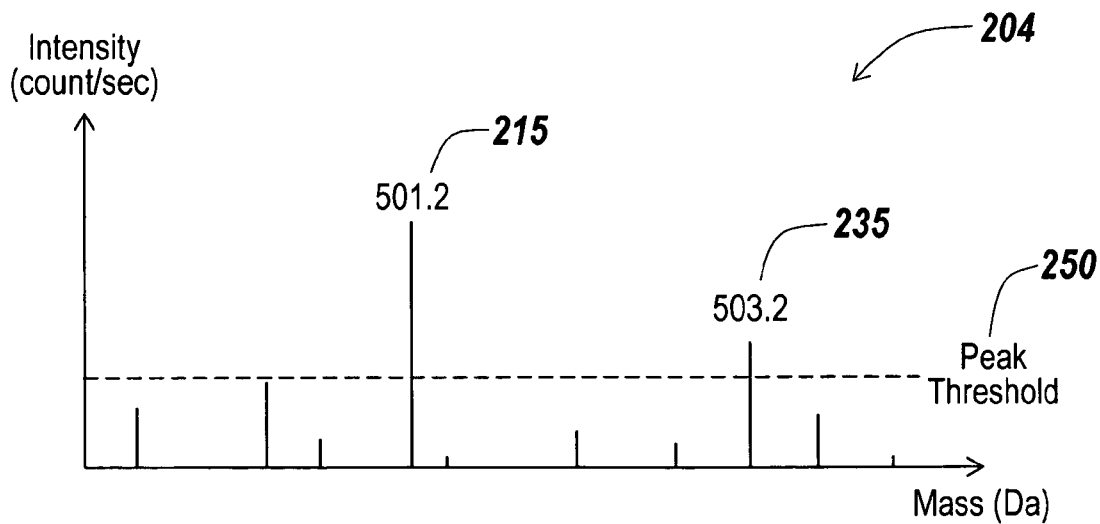
FIG. 9 illustrates a peak threshold criterion according to the illustrative embodiment of the invention.

A further variation of criteria that can be used in accordance with the invention is illustrated in FIG. 9. A graph 204 illustrates a peak threshold 250. A first mass value 215 and a second mass value 235 are illustrated. In the present example, because the first mass value 215 and the second mass value 235 each exceed the peak threshold 250, both the first mass value 215 and the second mass value 235 will be considered to be masses of interest. Other mass intensity values that do not exceed the peak threshold 250 would not be considered to represent masses of interest.

Figure 10:
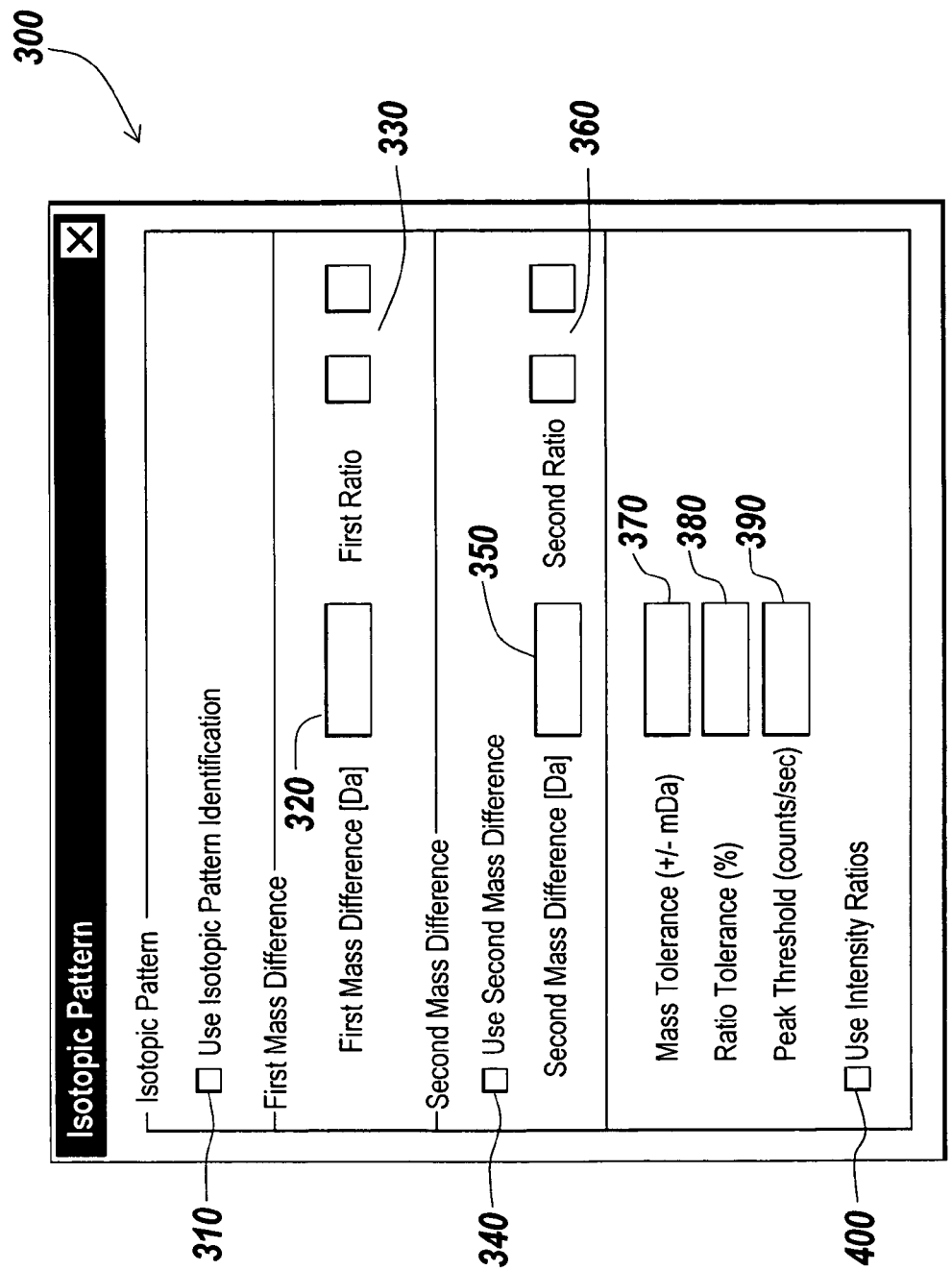
FIG. 10 illustrates a user interface according to the illustrative embodiment of the invention.

FIG. 10 illustrates an example of a user interface 300 that may be used with the illustrative embodiment of the invention. FIG. 11 provides a table 400 illustrating default values that may be used in accordance with the illustrative embodiment of the invention. The user interface 300 includes the ability to activate the analysis of mass intensity values to find those of interest. In order to activate this process, the use of isotopic pattern identification 310 is checked. It is noted that FIG. 11 specifies that the use of isotopic pattern identification 310 is defaulted to false. This default may be used when it is desirable to require the user to activate the analysis activity. If a first mass difference 320 criteria is desired, a first mass difference may be specified. If a first ratio 330 is desired, it may also be specified. If the use of the second mass difference 340 is specified, a second mass difference 350 and/or a second ratio 360 may be specified. In order to activate the use of the first ratio 330 or second ratio 360, the use of intensity ratio 400 must be specified. A mass tolerance 370 or ratio tolerance 380 may also be specified, as desired. Alternatively, or in addition, a peak threshold 390 may be specified.

It is understood that the user interface 300 of FIG. 10 is an example and a wide variety of alternatives are within the scope of the invention. It is understood that the default values as noted in table 400 of FIG. 11, are merely provided as a non-limiting example and that a wide variety of default values, ranges, units, and fields are within the scope of the invention.

Figure 12:
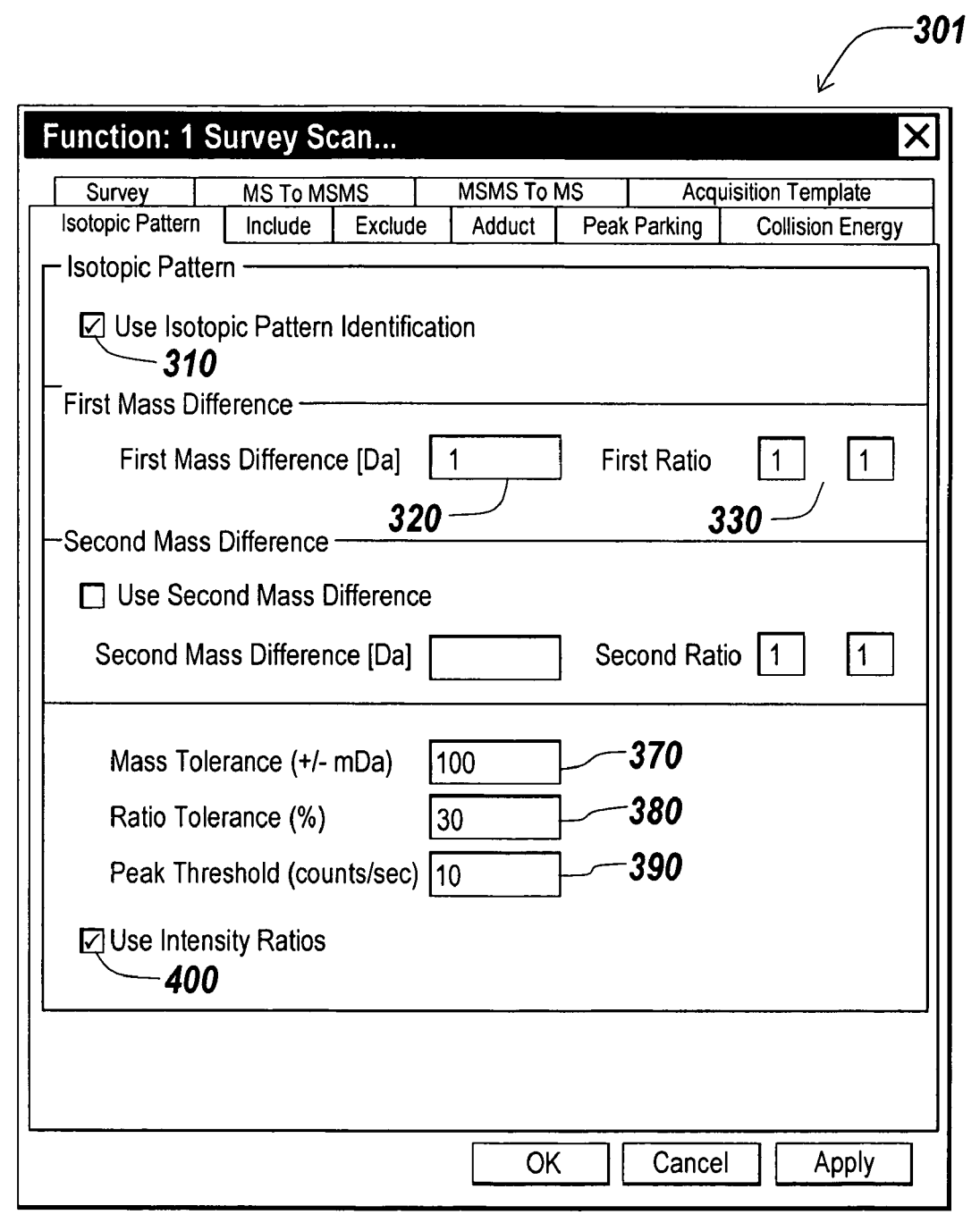

FIG. 12 provides a further example of the user interface 301 according to an example of implementation of an embodiment of the invention. According to the example of FIG. 12, the use of isotopic pattern identification 310 is specified. The use of a first mass difference 320 of 1 Da is specified and use of a first ratio 330 has been activated 400. Furthermore, a mass tolerance 370 of 100 mDa has been specified along with a 30% ratio tolerance 380. A further criteria that must be met for a mass intensity value of interest, according to the example, is an intensity threshold 390 of 10 counts per second.

Various embodiments of the invention can be used both in a single injection and other MS to MS/MS functions, such as survey, precursor ion scanning and neutral loss scanning functions, of a Qtof mass spectrometer, such as the MICRO-MASS® Q-Tof micro™ mass spectrometer. Embodiments of the invention can be used to act as a filter, alone or in combination with other filters, for a switch from MS to MS/MS. The invention may also be employed in post-processing or real-time processing. Examples of such processing include the continuum acquisition mode (post-processing) in the centroid (real-time) acquisition modes of a Qtof mass spectrometer, such as the MICROMASS® Q-Tof micro™ mass spectrometer.

Figure 13:
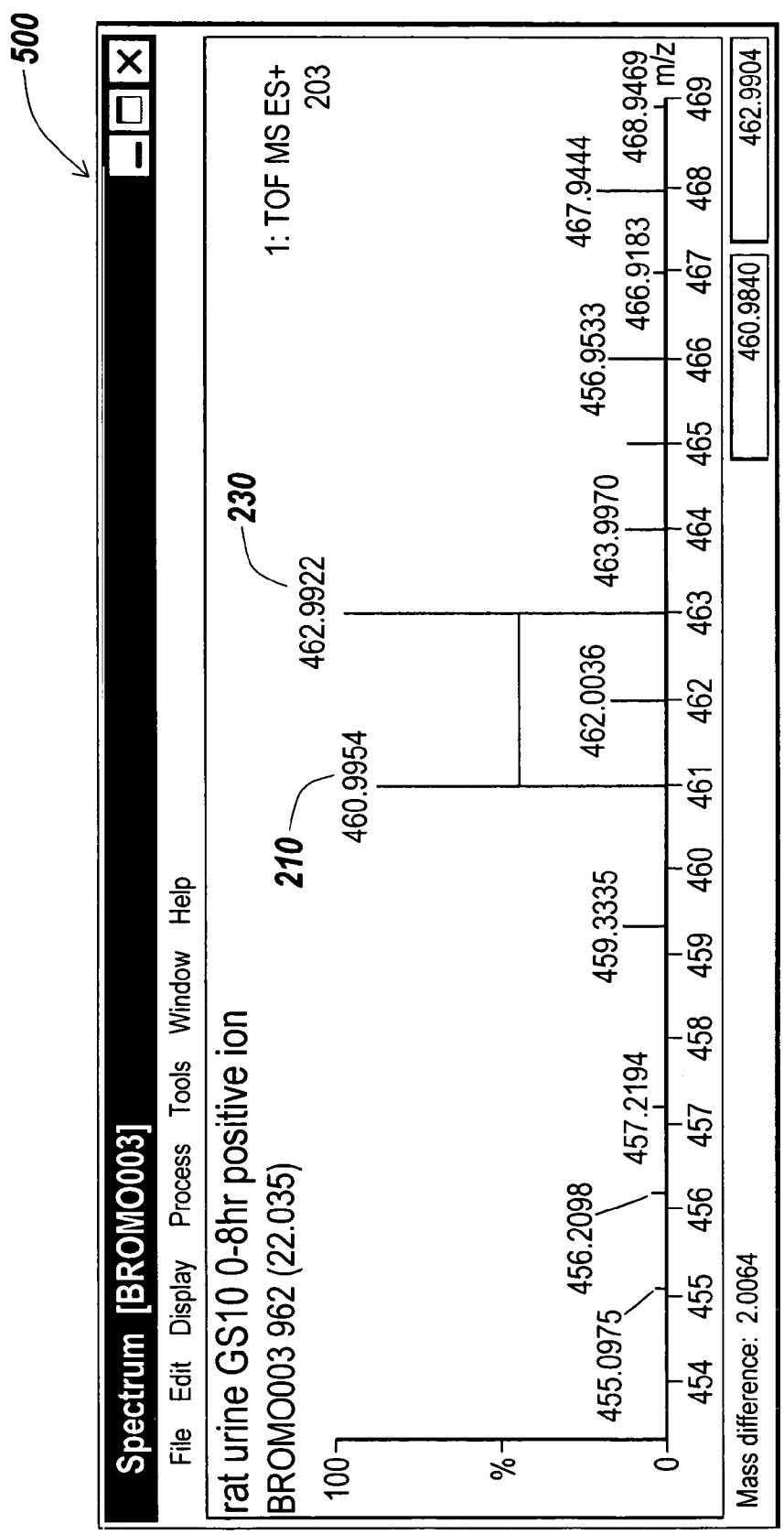
FIG. 13 provides a graph having a plurality of mass intensity values according to an example of the illustrative embodiment of the invention.

FIG. 13 illustrates an example of a plurality of mass intensity values displayed on a graph 500. In the example, criteria settings have been defined as a first mass difference of 2 Da, a mass tolerance of +/−25 mDa, a first ratio of 1:1, and a ratio tolerance of +/−10%. In the example, both a first mass 210 of 460.9954 Da and a second mass 230 of 462.9922 Da are considered masses of interest.

Those skilled in the art will recognize that the mass intensity values may be saved in a database where they can be reviewed later to verify the accuracy of the analysis.

The illustrative embodiment of the present invention may be used in a wide variety of applications, such as to identify impurities in a drug sample. Similarly, it may also be used to enforce patent rights by analyzing the by-products of a chemical reaction in order to diagnose a possible chemical infringer. Additionally, various embodiments of the present invention may also be used to analyze natural products and to determine their purity level. Those skilled in the art will recognize that the analysis system revealed herein may use analysis system components other than mass spectrometry to analyze the analyte sample and that gas chromatography may be substituted for liquid chromatography without departing from the scope of the present invention.

The present invention has been described by way of example, and modifications and variations of the exemplary embodiments will suggest themselves to skilled artisans in this field without departing from the spirit of the invention. Features and characteristics of the above-described embodiments may be used in combination. The preferred embodiments are merely illustrative and should not be considered restrictive in any way. The scope of the invention is to be measured by the appended claims, rather than the preceding description, and all variations and equivalents that fall within the range of the claims are intended to be embraced therein.

Having described the invention, what is claimed as new and protected by Letters Patent is:

1. In an isotopic signature with mass analysis system, a method comprising the steps of:
    obtaining a plurality of mass intensity values corresponding to a plurality of masses;
    comparing said plurality of mass intensity values to a criteria to determine whether any of said plurality of masses are of interest; and
    directing that a mass spectrometry process be performed on any of said plurality of masses that are of interest.

2. The method of claim 1, wherein, before said step of comparing, the step of obtaining at least a portion of said criteria by the use of a user interface.

3. The method of claim 1, wherein said isotopic signature analysis system is a liquid chromatography-mass spectrometry-mass spectrometry system.

4. The method of claim 1, wherein said criteria comprises a first mass difference between a first mass and a second mass.

5. The method of claim 4, wherein said criteria further comprises a second mass difference between said first mass and a third mass.

6. The method of claim 4, wherein said criteria further comprises a peak threshold.

7. The method of claim 4, wherein said criteria further comprises a first ratio between an intensity of said first mass value and an intensity of said second mass value.

8. The method of claim 1, wherein said criteria comprises a first ratio between an intensity of a first mass value and an intensity of a second mass value.

9. The method of claim 8, wherein said criteria further comprises a second ratio between said intensity of said first mass value and an intensity of a third mass value.

10. The method of claim 8, wherein said criteria further comprises a peak threshold.

11. The method of claim 1, wherein said criteria comprises a peak threshold.

12. The method of claim 1, wherein said plurality of masses of said step of obtaining are exact masses.

13. A medium holding computer executable steps for a method, said method comprising the steps of:
    obtaining a plurality of mass intensity values corresponding to a plurality of masses;
    comparing said plurality of mass intensity values to a criteria to determine whether any of said plurality of masses are of interest; and
    directing that a mass spectrometry process be performed on any of said plurality of masses that are of interest.

14. The medium of claim 13, wherein, before said step of comparing, the step of obtaining at least a portion of said criteria by the use of a user interface.

15. The medium of claim 13, wherein said criteria comprises a first mass difference between a first mass and a second mass.

16. The medium of claim 13, wherein said criteria comprises a first ratio between an intensity of a first mass value and an intensity of a second mass value.

17. The medium of claim 13, wherein said criteria comprises a peak threshold.

18. The medium of claim 13, wherein said plurality of masses of said step of obtaining are exact masses.

19. A system for analysis of isotopic signature with exact mass, said system comprising:
    an electronic device adapted to obtain a plurality of mass intensity values corresponding to a plurality of masses and compare said plurality of mass intensity values to a criteria to determine whether any of said plurality of masses are of interest; and
    a second stage mass separation device to perform mass spectrometry on any of said plurality of masses that are of interest.

20. The system of claim 19, wherein said criteria comprises a first mass difference between a first mass and a second mass.

21. The system of claim 19, wherein said criteria comprises a first ratio between an intensity of a first mass value and an intensity of a second mass value.

22. The system of claim 19, wherein said criteria comprises a peak threshold.

23. The system of claim 19, wherein said plurality of masses are exact masses.

* * * * *